US00PP20509P3

(12) United States Plant Patent
Warren et al.

(10) Patent No.: US PP20,509 P3
(45) Date of Patent: Nov. 24, 2009

(54) CALLA LILY PLANT NAMED 'ROSA BLZ'

(50) Latin Name: ***Zantedeschia* spp.**
Varietal Denomination: Rosa BLZ

(75) Inventors: Andrew G. F. Warren, Tauranga (NZ); Jacobus P. Spaans, Tauranga (NZ)

(73) Assignee: Bloomz Ltd, Tauranga (NZ)

( * ) Notice: Subject to any disclaimer, the term of this patent is extended or adjusted under 35 U.S.C. 154(b) by 278 days.

(21) Appl. No.: 11/787,992

(22) Filed: Apr. 18, 2007

(65) Prior Publication Data

US 2008/0263735 P1 Oct. 23, 2008

(51) Int. Cl.
*A01H 5/00* (2006.01)

(52) U.S. Cl. ..... Plt./490
(58) Field of Classification Search ..... Plt./490
See application file for complete search history.

(56) References Cited

OTHER PUBLICATIONS

Upov Plant Variety Database 2008/05 p. 1.*

* cited by examiner

*Primary Examiner*—Annette H Para
(74) *Attorney, Agent, or Firm*—Jondle & Associates, P.C.

(57) ABSTRACT

A calla lily plant particularly distinguished by a red-purple spathe with darker red-purple veins, medium density maculation of the leaves that is visible from both sides and which produces 2 to 3 inflorescences per 3-cm tuber, is described.

2 Drawing Sheets

Genus and species: *Zantedeschia* spp.
Variety denomination: 'Rosa BLZ'.

BACKGROUND OF THE NEW PLANT

The present invention comprises a new and distinct cultivar of calla lily, botanically known as *Zantedeschia* spp., and hereinafter referred to by the cultivar name 'Rosa BLZ'. The new cultivar was asexually reproduced by micropropagation resulting from the cross of the female parent an unnamed seedling of *Zantedeschia* spp. (unpatented) with a red-purple spathe and the male parent, an unnamed seedling of *Zantedeschia* spp. (unpatented) with a pink spathe.

The new cultivar was created in Tauranga, New Zealand and has been asexually reproduced repeatedly by micropropagation in India over a two-year period. The present invention has been found to retain its distinctive characteristics through successive propagations.

Plant Breeder's Rights for this cultivar were applied for in New Zealand on Feb. 13, 2006 and granted on May 3, 2007. Community Plant Variety Rights for this cultivar were applied for in Europe on Aug. 4, 2006 and granted on Apr. 6, 2009.

SUMMARY OF THE INVENTION

The following are the most outstanding and distinguishing characteristics of this new cultivar when grown under normal horticultural practices in Tauranga, New Zealand.

1. A red-purple spathe with darker red-purple veins;
2. Medium density maculation of the leaves that is visible from both sides; and
3. Produces 2 to 3 inflorescences per 3-cm tuber.

DESCRIPTION OF THE PHOTOGRAPHS

This new calla lily plant is illustrated by the accompanying photographs which show the mature inflorescence and foliage of the plant. The colors shown are as true as can be reasonably obtained by conventional photographic procedures.

Figure 1:
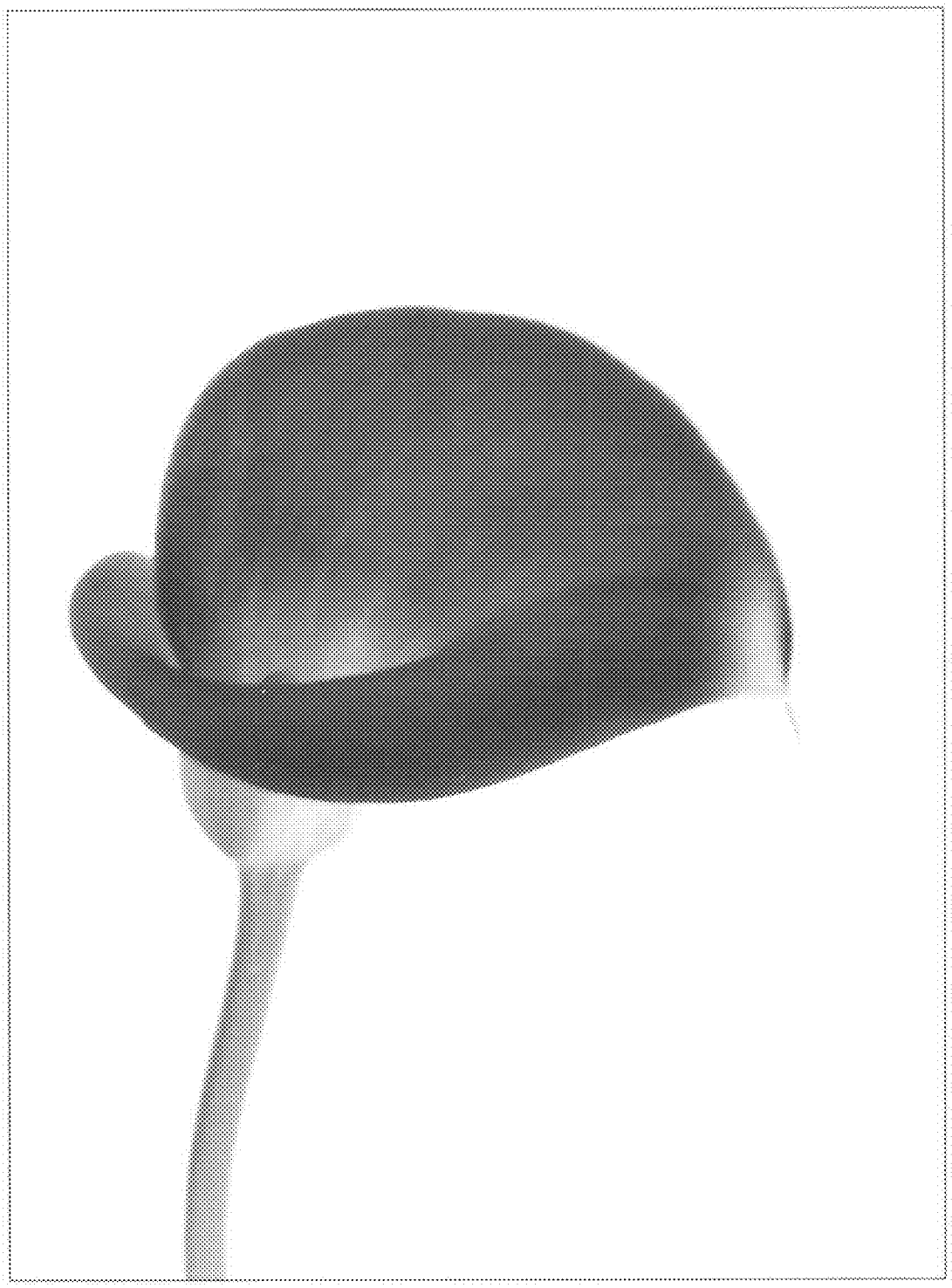
Figure 2:
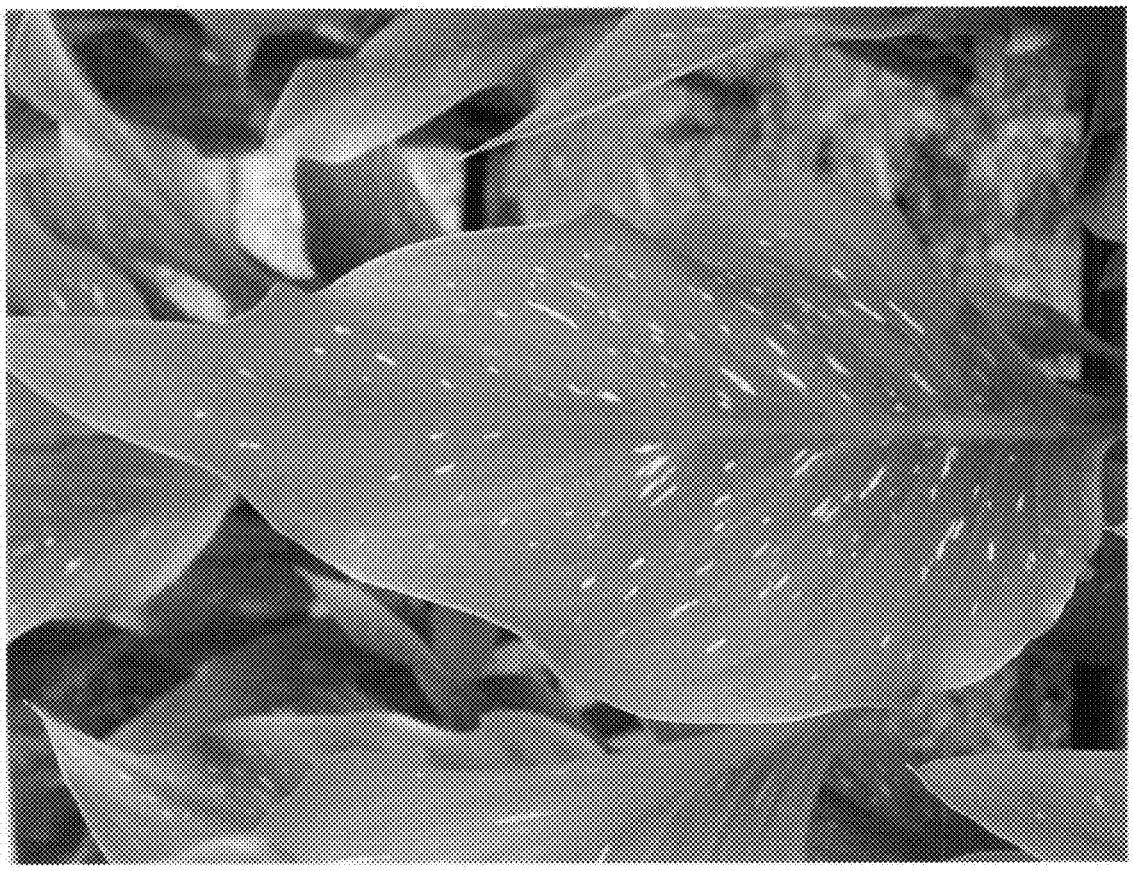

FIG. 1 shows a close-up of the mature inflorescence.
FIG. 2 shows a close-up of a mature leaf with maculation.

DESCRIPTION OF THE NEW CULTIVAR

The following detailed description sets forth the distinctive characteristics of 'Rosa BLZ'. The data that define these characteristics were collected from asexual reproductions carried out in Tauranga, New Zealand. The plant history was taken on two-year-old plants based on a 3-cm diameter tuber under New Zealand summer conditions. Color references are primarily to The R.H.S. Colour Chart of The Royal Horticultural Society of London (RHS).

DETAILED BOTANICAL DESCRIPTION

Classification:
- *Family.*—Araceae.
- *Botanical name.*—*Zantedeschia* spp.
- *Common name.*—Calla lily.

Plant:
- *Form.*—Erect.
- *Height of the leaf canopy above the soil.*—45 cm to 60 cm.
- *Height of top of inflorescence above the soil.*—50 cm to 65 cm.
- *Diameter.*—25 cm to 40 cm.
- *Number of inflorescences per tuber size.*—Tuber diameter 3 cm: 2 to 3 Tuber diameter 4 cm: 3 to 5 Tuber diameter 5 cm: More than 5.
- *Time to produce a finished flowering plant.*—6 to 10 weeks depending on the climate and environment.
- *Lastingness of inflorescence on the plant.*—2 to 3 weeks.

Growing points:

*Average number per plant.*—1 to 3.

*Character.*—Strong.

*Color.*—Upper surface: RHS 137C Lower surface: RHS 146C Base: RHS 155D.

Leaves:

*Size.*—Width: 8 cm to 12 cm Length: 23 cm to 30 cm.

*Shape.*—Ovate.

*Color.*—Upper surface: RHS 137A Lower surface: RHS 137C.

*Maculation* (*leaf spots*).—General: Maculation is only on the upper surface of the leaf but is visible from the lower surface Density: Medium density Color: RHS 155C (white).

*Apex.*—Acute to apiculate.

*Base.*—Attenuate to shortly attenuate.

*Margin.*—Entire, moderately wavy.

*Margin color.*—Green.

*Venation pattern.*—Pinnate.

*Surface texture.*—Leathery.

*Petiole.*—Average number per tuber: 6 to 10 Length: 27 cm to 33 cm Diameter: 0.6 cm to 1.2 cm Color:

Upper portion: RHS 137C Base: RHS 146C Texture: Smooth Character: Strong Sheath: Width: 0.7 cm to 0.9 cm Length: 6 cm to 8 cm Color: RHS 146B.

Roots:

*Color.*—RHS 155D (white).

*Branching.*—Not branched, attached to the top of the tuber at apices.

Inflorescence:

*Spathe* (*flower body*).—Size: Height: 8 cm to 10 cm Width: 5 cm to 6 cm Color: Upper part: RHS 60A Lower part: RHS 60C Veins: RHS 59A Shape: Round Texture: Smooth Apex: Caudate Base: Attenuate Margin: Entire Fragrance: Absent.

*Spadix* (*reproductive organs*).—Size: Length: 2.5 cm to 3.5 cm Diameter: 0.5 cm to 0.7 cm Color: Base: RHS 65B Upper: RHS 53C Position relative to spathe: Upright Shape: Elongated Apex: Rounded.

*Peduncle* (*flower stem*).—Length: 35 cm to 55 cm Diameter: 0.7 cm to 0.9 cm Color: Base: RHS 155A Upper part: RHS 146B Texture: Smooth Strength: Strong.

Reproductive organs:

*Location of female organs.*—Basal position of the spadix.

*Location of male organs.*—Upper position of the spadix.

*Perianth* (*the floral envelope, calyx and corolla*).—Conspicuous.

*Stamens.*—Not visible before pollen release.

*Pollen color.*—Light-yellow.

*Pistil.*—Number: 25 to 35 per spadix Color: RHS 17B.

Fruit:

*General.*—Whole fruit is 3.0 cm to 4.0 cm wide and 4.5 cm to 5.5 cm long;

individual berries are round and 0.5 cm to 0.7 cm in circumference.

*Number.*—8 to 15 per plant.

*Color.*—Green.

Disease and insect resistance:

*Disease resistance.*—No susceptibility noted to date.

*Pest resistance.*—No susceptibility noted to date.

COMPARISON WITH PARENTAL AND COMMERCIAL CULTIVARS

When the instant plant is compared to the female parent, an unnamed seedling of *Zantedeschia* spp. (unpatented), 'Rosa BLZ' has a more intense red-purple spathe color and more inflorescences per plant than the female parent.

When 'Rosa BLZ' is compared to the male parent, an unnamed seedling of *Zantedeschia* spp. (unpatented), 'Rosa BLZ' has a taller plant habit than the male parent.

'Rosa BLZ' differs from the commercial cultivar 'Red Sox' (U.S. Plant Pat. No. 14,063) in that 'Rosa BLZ' has a red-purple spathe, while 'Red Sox' has a greyed-red to greyed-purple spathe. Additionally, 'Rosa BLZ' has ovate-shaped leaves, while 'Red Sox' has lanceolate-shaped leaves.

It is claimed:

1. A new and distinct cultivar of calla lily plant, as described and shown herein.

* * * * *